United States Patent [19]

Dore et al.

[11] 4,416,662
[45] Nov. 22, 1983

[54] ROLLER INFUSION APPARATUS

[75] Inventors: Charles F. G. Dore, Harrow; Geoffrey R. Chambers, Northwood, both of England

[73] Assignee: The United States of America as represented by the Department of Health and Human Services, Washington, D.C.

[21] Appl. No.: 271,271

[22] Filed: Jun. 8, 1981

[30] Foreign Application Priority Data

Jun. 13, 1980 [GB] United Kingdom ............... 8019431

[51] Int. Cl.³ ............................................. A61M 37/00
[52] U.S. Cl. ................................................... 604/154
[58] Field of Search ......... 128/218 A, DIG. 1, 214 F, 128/DIG. 12, 218 F, 218 N, 218 NV; 401/176, 179, 182, 171, 172, 174, 181; 222/309, 333, 326, 327; 604/131, 134, 151, 152, 154, 155, 209, 210, 224

[56] References Cited

U.S. PATENT DOCUMENTS

| | | | |
|---|---|---|---|
| 1,892,485 | 12/1932 | Du Four | 172/120 |
| 2,768,623 | 10/1956 | Marchand | 128/218 |
| 3,198,385 | 8/1965 | Maxwell | 222/333 |
| 3,336,925 | 8/1967 | Thompson | 128/218 A |
| 3,415,419 | 12/1968 | Jewett et al. | 128/218 A |
| 3,456,649 | 7/1969 | Jewett . | |
| 3,833,030 | 9/1974 | Waldbauer, Jr. | 222/309 |
| 3,838,688 | 10/1974 | May et al. | 128/214.4 |
| 3,923,060 | 12/1975 | Ellinwood, Jr. | 128/DIG. 1 |
| 3,993,064 | 11/1976 | McCarthy et al. | 128/218 A |
| 3,993,065 | 11/1976 | Szabo et al. | 128/DIG. 12 |
| 4,269,185 | 5/1981 | Whitney et al. | 128/214 F |

FOREIGN PATENT DOCUMENTS 2419052 11/1973 Fed. Rep. of Germany .
1465653 12/1965 France .
1528385 10/1978 United Kingdom .

Primary Examiner—John D. Yasko
Assistant Examiner—J. L. Kruter
Attorney, Agent, or Firm—Browdy and Neimark

[57] ABSTRACT

An infusion apparatus consisting of a housing containing an electric motor, the housing having a channel-shaped chassis integrally connected thereto and laterally offset therefrom. A toothed drive roller is transversely journalled in the chassis and is drivingly coupled to the motor by meshing bevel gears. The chassis side walls have opposing vertical grooves receiving the peripheral radial flange of the barrel of a syringe, holding the barrel so that its plunger is transversely engaged on the toothed drive roller. A clamping rod is pivoted to the upper portion of one of the side walls and is lockingly engageable with the other side wall. The clamping rod carries a pressure pad which clampingly engages on the plunger to hold it in driving engagement with the toothed roller. A cannula is detachably connected to the discharge end conduit of the barrel. The discharge conduit is provided with a needle penetrable through a self-closing septum provided in the cannula connector member. The leading end of the cannula may be formed with a solid reduced end suture connectable to a needle which can be passed through a patient's skin tissue to draw the cannula with it. The cannula is formed with a slit adjacent the suture portion to allow air expulsion and then drug expulsion after the cannula has been adjusted to locate the slit subcutaneously.

25 Claims, 8 Drawing Figures

ROLLER INFUSION APPARATUS

FIELD OF THE INVENTION

This invention concern infusion apparatus and more particularly such apparatus which is powered for operation over long periods.

BACKGROUND OF THE INVENTION

Much interest has arisen during recent years in the development of the last-mentioned apparatus for the infusion of drugs in a relatively continuous manner compared to the conventional intermittent form of administration by syringe injection, such infusion affording closer treatment control, allowing a reduction of overall drug dosage in many cases, and providing other benefits. Typically, the powered infusion apparatus in question has involved an incremental drive by a battery-powered motor, through a nut-and-leadscrew mechanism, to push the free end of the plunger of a syringe coupled to the patient by way of a cannula. Examples of such motor driven apparatus are described in UK Pat. No. 1,528,385 and these examples have been used successfully with standard syringes to provide individual discharge periods of up to 48 hours.

It is evident that the benefits of apparatus such as that just described would be improved by extension of the discharge period for an individual syringe, up to the order of a week or more, say, but this is problematical. Difficulty arises particularly when initiating operation after loading a syringe in the apparatus insofar as infusion does not commence until backlash in the drive system has been taken up and such movements represent a significant drive period. While the backlash can be virtually eliminated in much of the drive system, the nut-and-leadscrew mechanism normally involves the use of a releasable half nut which allows free leadscrew movement to facilitate syringe loading, and the subsequent re-engagement of the nut introduces a variable amount of backlash between the leadscrew and syringe plunger.

SUMMARY OF THE INVENTION

An object of the present invention is to obviate this difficulty and, to this end, the invention provides apparatus similar to that discussed generally above but in which the drive mechanism involves a roller drivably engageable with the side of a syringe plunger. The provision of such a drive arrangement need introduce no backlash when engaged with a syringe plunger, it allows the provision of a more compact apparatus compared to one involving a leadscrew, and the roller can be engaged with the plunger close to the associated syringe barrel without any need for adjustment to take account of variation of plunger position with syringe charge as is the case with a leadscrew.

It is preferred that the roller be of toothed form to avoid slippage on the syringe plunger, the toothing suitably extending axially across the roller in the manner of a pinion gear wheel. Since the syringe will normally be a disposable form made in plastics material, and the roller of metal, the toothing is further advantageous in penetrating the plunger to leave a record of the drive progress.

Also, bearing in mind this question of materials, it is further preferred that successive teeth of the roller be separated by smooth bottom lands which engage on the plunger with the teeth fully penetrated. Use of the drive arrangement when engaged in this way serves to maintain the mechanical advantage of the roller drive substantially constant, which is important in relation to the error which may otherwise accumulate during a long discharge period.

BRIEF DESCRIPTION OF THE DRAWINGS

The above-discussed features of the present invention will be clarified, and other features thereof made evident, by the following description by way of example with reference to the accompanying drawings, in which.

DESCRIPTION OF PREFERRED EMBODIMENT

Figure 1:
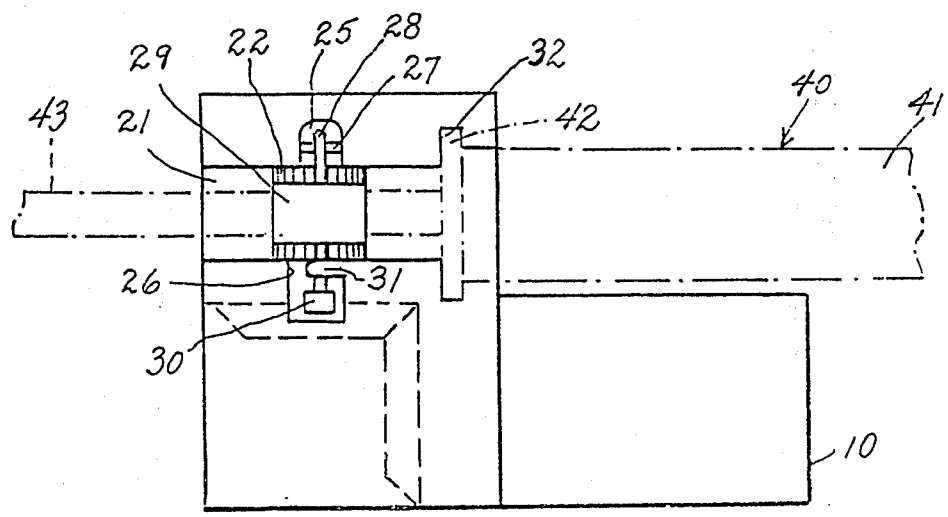
FIGS. 1 to 4 respectively diagrammatically illustrate one embodiment of apparatus according to the invention in plan, side end and perspective views, respectively.

The apparatus of FIGS. 1 to 4 comprises a housing 10 containing a motor 11, a gearbox 12 drivably connected to the motor and having an output shaft 13 extending from one end of the housing, control circuit 14, for regulating the operation of the motor, and a battery power source 15 for energising the motor by way of the control circuit. The free end of the output shaft has a bevel gear 16 fixed thereon.

The apparatus in question further comprises a chassis 20 connected with the housing 10 and projecting from the output end thereof. The chassis is of a generally open-ended trough form off-set relative to the housing, with the trough cavity 21 extending longitudinally parallel to the output shaft 13 but to one side of the housing.

A toothed drive roller 22 is carried in bearings 23 at its ends, the bearings being mounted in respectively opposed side walls of the chassis 20 to locate the roller with its axis extending transversely across the cavity 21 and in the lower zone thereof. The end of the roller 22 nearer to bevel gear 16 projects through its bearing and the surrounding side wall of the chassis, and itself carries a bevel gear 24 engaged with the similar gear 16.

The side walls of the chassis 20 are recessed at 25 and 26 above the bearings 23 further from and nearer to bevel gear 24, respectively. A pin 27 is secured across the recess 25, and a rod 28 is pivotally connected at one end to this pin for movement between a first position extending transversely across the cavity 21 and a second, upstanding position leaving the cavity open from above. The rod 28 carries a pressure pad 29 partway therealong and a knob 30 at its free end, the pad and knob respectively entering the cavity 21 and recess 26 when the rod is in its first position. The recess 26 has a bar 31 extending partway thereacross and around which the rod can be latched in its first position, with the knob 30 sited behind the bar.

The side walls of the chassis 20 are further recessed in opposed manner towards the end of the cavity 21 nearer to the housing 10, this recessing involving like slots 32.

Use of this apparatus involves an associated syringe which is indicated in FIG. 1 in broken outline at 40 and comprises a barrel 41, a radial flange structure 42 at one end of the barrel, and a plunger 43 projecting from the same end of the barrel. The syringe is operably coupled with the apparatus as evident from FIG. 1 by locating parts of the flange 42 in the slots 32 of the chassis 20, with the main body of the barrel 41 extending alongside the housing 10, and with the plunger 43 extending along the chassis cavity 21 to project from the further end thereof from the slots 32.

Clearly the rod 28 is moved to its upstanding position to effect this location, and the rod is thereafter lowered and latched in recess 26 to grip the plunger between the drive roller 22 and the pressure pad 29. Operation of the coupled apparatus and syringe then simply involves energisation of the motor through its control circuit to rotate, by way of the gearbox and bevel gears, the drive roller in the appropriate direction to drive the syringe plunger into its syringe.

Clearly, for this use and operation, the overall forms of the chassis and syringe need to be suitably relatively proportioned and dimensioned to allow the desired mutual coupling. More particularly, the syringe barrel should be firmly held against axial movement by the location of the flange in the related chassis slots, and the syringe plunger should be held firmly between the roller and pressure pad to ensure non-slipping drive.

Figure 8:
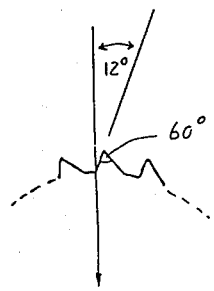
FIG. 8 is a partial detail view of the roller teeth.
Figure 2:
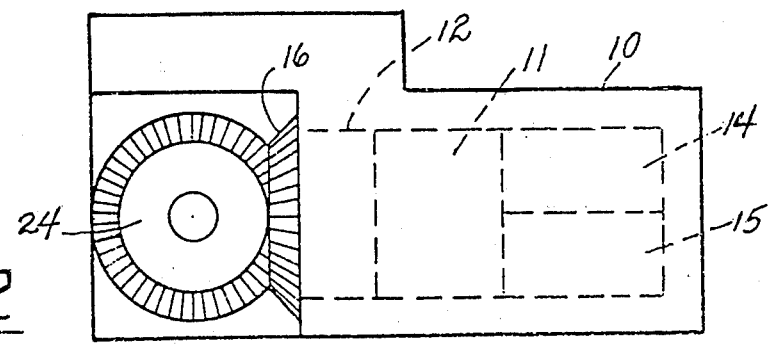
Figure 3:
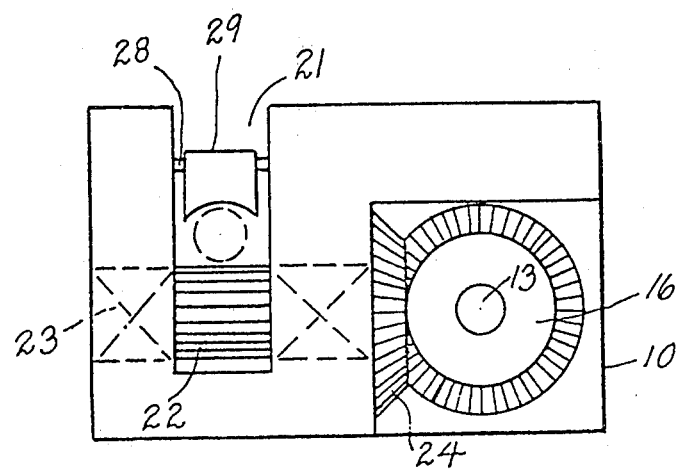
Figure 4:
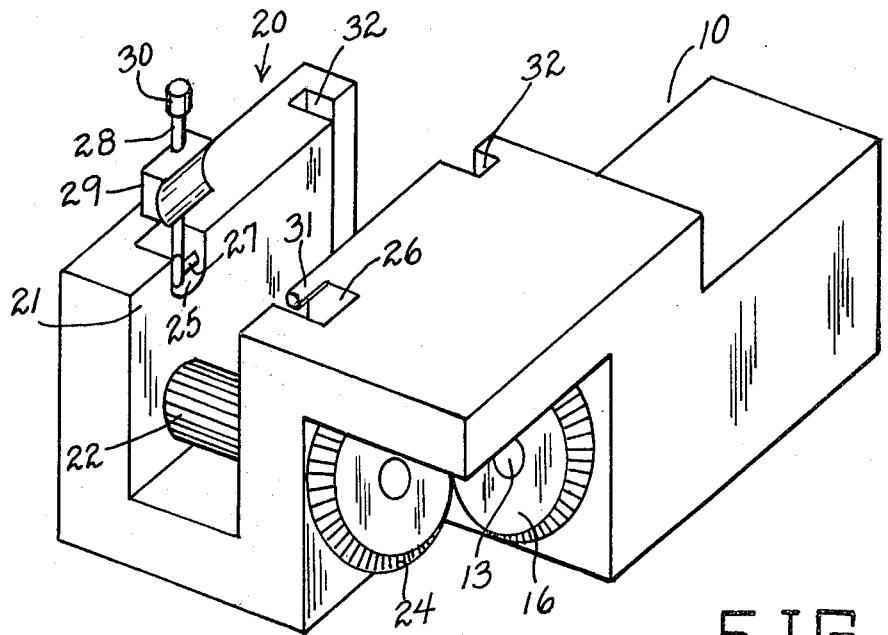

In this last connection it has already been mentioned above that the syringe is suitably of a disposable plastics material construction and the roller of metal so that the teeth of the latter penetrate the syringe plunger to ensure a non-slipping drive. It has further been noted that the roller preferably has teeth extending axially thereacross in the manner of a pinion gear wheel, with successive teeth being spaced by smooth bottom lands which engage on the plunger with the teeth fully penetrated. Such penetration maintains the mechanical advantage of the roller drive action substantially constant and is effected by suitable choice of latching force relative to the plastics material hardness. Development of the present invention to date indicates no undue difficulty in achieving this result in a repeatable manner with syringes made of the previously used plastics materials such as polypropylene. However, this development has at the same time indicated preferred configurations for the drive roller toothing, namely, that the teeth should be substantially triangular in profile with an apex angle of about 60° and negative rake of approximately 12° as shown in FIG. 8.

It is also desirable that the syringe be as rigid as possible, compatable with other requirements, and this leads to a preferment for a circular cylindrical form for both the barrel and plunger. If the flange is also of circular disc form, the syringe can be loaded in the apparatus in any circumferential orientation. Such a syringe differs in detail from those currently in routine use and, given that a special form of syringe is preferred, it is appropriate to consider other improvements relevant to the intended usage in the present instance.

One such improvement concerns the fact that while a subcutaneous plastics cannula can be left in situ in a patient for a very long period, it is normally necessary to disconnect the powered infusion apparatus and syringe at intervals within this period. Obviously it is necessary to disconnect the syringe when empty, and it is appropriate to disconnect the infusion apparatus for bathing and in other circumstances. Reconnection can involve some difficulties with the use of a conventional syringe and cannula, and it is proposed that the reconnection situation be improved by use of a syringe and cannula with co-operating terminal fittings as shown in FIG. 5 of the drawings.

Figure 5:
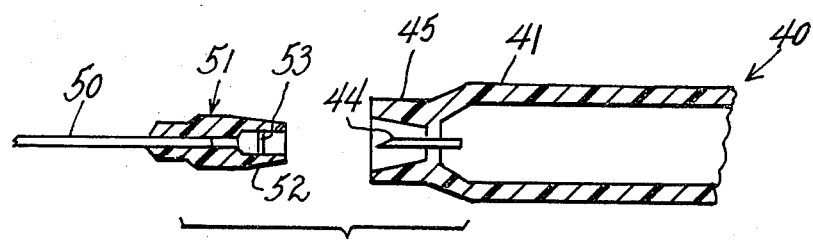
FIG. 5 illustrates co-operating terminal fittings for a syringe and cannula for use with the apparatus of FIGS. 1 to 4.

In FIG. 5 the syringe 40 is shown with the forward end of its barrel 41 terminating in a needle 44 located in an annular projection 45 of which the interior is formed to a Luer conical taper. The associated cannula is indicated at 50 and has its end secured in a terminal member 51 which diverges at its free end into an annular portion 52 of which the exterior is formed to a Luer conical taper complementary with that of the syringe. The wall thickness of the portion 52 is such as to engage in the space between the syringe projection 45 and needle 44, and the portion 52 is transversely closed partway therein by a septum 53 of silicon rubber or other C terminal fitting the syringe and cannula are readily connected and disconnected without difficulty, and that the cannula is closed whenever the syringe is disconnected.

A further difficulty associated with the use of powered infusion apparatus is associated with cannula location and securement in the patient.

In one existing procedure use is made of a hypodermic needle with a bore of sufficient size for passage of the cannula therethrough. The needle is located in the patient, the cannula fitted in the needle, and the infusion apparatus is connected and air expelled from the cannula before the needle is extracted and the cannula isolated. The difficulty is that the needle must be removed forwardly and, by virtue of its size, causes such trauma that local anaesthetics are normally required.

In another existing procedure a similar needle is used but which can be longitudinally split following rearward withdrawal. However, safe infusion apparatus connection and air expulsion are difficult with such a needle.

Two improved procedures are proposed here.

Figure 6:
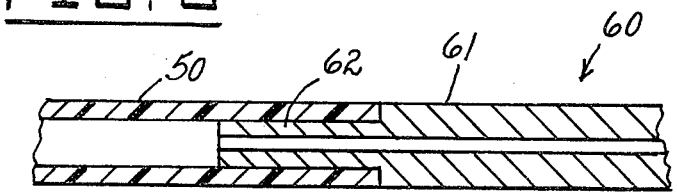
FIGS. 6 and 7 illustrate respectively different arrangements for cannula location in a patient with use of the apparatus of FIGS. 1 to 4.

In the first such procedure a needle 60 such as shown in FIG. 6 is employed. This needle has a main, leading portion 61 of the same outside diameter as the cannula 50 and a rearward portion 62 of outside diameter complementary to the inside diameter of the cannula. In use the rear portion is located in the cannula bore and the then smooth needle-cannula combination can be inserted in the patient, the infusion apparatus connected, air expelled, and the needle then withdrawn and disconnected to leave the open end of the cannula located subcutaneously.

Figure 7:
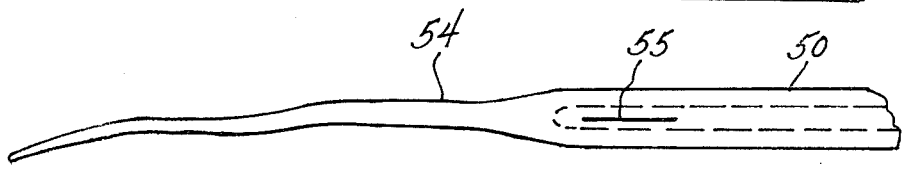

In the second such procedure use is made of a cannula 50 shown in FIG. 7 and which is formed at its leading end to a solid suture portion 54 which can then be located by a conventional needle passed through the patient to draw the cannula with it. The suture portion can then be knotted to hold the cannula in place. The cannula is additionally formed with a slit 55 in its hollowed portion adjacent the suture, which slit allows air expulsion after initial location of the cannula, and then drug expulsion after slight withdrawal to locate the slit subcutaneously.

While the present invention has been described with more particular reference to the illustrated embodiments, it will be appreciated that it is not intended to be limited thereby but is capable of variation. For example, the drive roller of the illustrated apparatus co-operates with a pressure pad but could co-operate with an opposed roller. Such an alternate drive arrangement may be appropriate to the use of a longitudinally finned syringe plunger, of cruciform cross-sectional shape, say. Also, the latching arrangement can involve alternatives to that shown, such as an eccentric cam or roller. Similarly, the bevel gear coupling to the drive roller is one option of many to variously suit differing overall housing/chassis configurations. Again, while the illustrated apparatus is designed for use with a particular, compatible syringe, adjustability to suit different standard syringes is a possibility.

No mention has been made of control circuit detail for the motor drive and this may be of any suitable form such as is already available or is developed for this purpose.

Lastly, while reference has been made to particular arrangements for syringe-cannula connection and cannula location, those arrangements are not essential to use of the infusion apparatus. However, insofar as these arragements are advantageous they represent present preferments and can find application with other forms of infusion apparatus than that.

What is claimed is:

1. An infusion apparatus comprising housing means, a motor mounted in said housing means, a channel-shaped chassis rigidly connected to said housing means and being laterally offset therefrom, a syringe having a barrel with a radial peripheral flange, a smooth-profiled plunger slidably engaged in said barrel, a drive roller means journalled in said channel-shaped chassis with the axis of said roller means being transverse to the length of said channel, said drive roller means having teeth projecting from the circumference thereof and adapted to penetratingly engage said smooth-profiled plunger to drive said plunger in said barrel, means drivingly coupling said motor to said drive roller means, and an annular discharge conduit projecting from the end of the barrel opposite said plunger, said chassis having parallel side walls formed with opposing grooves slidably receiving said peripheral flange and positioning said plunger to transversely engage on said drive roller means, abutment means mounted on said side walls and being clampingly engageable with said plunger to hold the plunger in driving engagement with said toothed roller means, and infusion cannula means communicatively connected to said discharge conduit.

2. The infusion apparatus of claim 1, and wherein said coupling means comprises meshing bevel gears connected respectively to the motor and the drive roller means.

3. The infusion apparatus of claim 1, and wherein said motor has an output shaft, and wherein said channel-shaped chassis has a trough cavity which extends parallel to said output shaft but is laterally offset therefrom.

4. The infusion apparatus of claim 1, and wherein said annular discharge conduit has a discharge needle mounted axially therein, and wherein said cannula means has a connection member sealingly engageable in said discharge conduit and provided with a transverse self-closing septum through which the needle is penetrable when the connection member is sealingly received in the conduit, and which closes when the connection member is detached from said discharge conduit.

5. The infusion apparatus of claim 1, and wherein an infusion needle is provided, said infusion needle having a main leading portion of substantially the same outside diameter as the cannula means and having a reduced rear portion fitting into the cannula means.

6. The infusion apparatus of claim 1, and wherein the cannula means is formed at its leading end with a solid reduced suture portion connectable to a needle which can be passed through the skin tissue of a patient to draw the cannula means with it, the cannula means being formed with a slit adjacent the suture portion to allow air expulsion and then drug expulsion after the cannula means has been adjusted to locate the slit subcutaneously.

7. An infusion apparatus comprising housing means, a motor mounted in said housing means, a channel-shaped chassis rigidly connected to said housing means and being laterally offset therefrom, a tubed drive roller means journalled in said channel-shaped chassis with the axis of said roller means being transverse to the length of said channel, means drivingly coupling said motor to said drive motor, a syringe having a barrel with a radial peripheral flange, a plunger slidably engaged in said barrel, and an annular discharge conduit projecting from the end of the barrel opposite said plunger, said chassis having parallel side walls formed with opposing grooves slidably receiving said peripheral flange and positioning said plunger to transversely engage on said drive roller means, abutment means mounted on said side walls and being clampingly engageable with said plunger to hold the plunger in driving engagement with said toothed roller means, said abutment means comprising a clamping rod pivoted to one side wall and being lockingly engageable with the other side wall of the pressure pad means on the rod engageable with the plunger, and infusion cannula means communicatively connected to said discharge conduit.

8. The infusion apparatus of claim 7, and wherein said clamping rod is pivoted to the upper portion of one side wall to swing in the vertical plane of the axis of the drive roller means.

9. The infusion apparatus of claim 8, and wherein the upper portion of said one side wall is formed with a recess provided with a longitudinally extending hinge pin, said clamping rod being rotatably mounted on said hinge pin.

10. The infusion apparatus of claim 9, and wherein said other side wall is formed with a second recess to receive the clamping rod and has a locking projection beneath which the clamping rod is lockingly receivable.

11. The infusion apparatus of claim 10, and wherein said clamping rod is provided with a pressure pad member located part way therealong and shaped to conformably engage on the plunger.

12. A powered medicinal infuser apparatus for infusing medicinals over long periods in a continuous manner comprising a housing carrying a toothed roller means, means for holding a disposable plastic syringe having a smoothly profiled plunger in predetermined disposition to said housing with said plunger extending transversely to the axis of rotation of and in driving penetrating engagement with said toothed roller, a motor for driving said toothed roller means, and a transmission operably coupling said motor and toothed roller means.

13. Apparatus according to claim 12 wherein the teeth of said roller means are, circumferentially of said roller means, of triangular shape with an apex angle of about 60° and a negative rake of about 12°.

14. Apparatus according to claim 12 wherein the teeth of said roller means are successively separated circumferentially of said roller means by smooth bottom lands.

15. Apparatus according to claim 12 wherein the teeth of said roller means extend axially thereacross.

16. Apparatus according to claim 12 wherein said syringe holding means comprises a pressure pad located in opposition about said plunger.

17. Apparatus according to claim 16 wherein said pad is movable between two positions, one of which separates the pad from said roller to release said plunger, and the other of which closes the pad towards said roller means to effect said driving engagement of the latter with said plunger.

18. Apparatus according to claim 12 wherein said motor has an output shaft, said housing has a longitudinal axis and holds said syringe with its longitudinal axis parallel with said motor output shaft, and said transmission includes a pair of mutually engaged bevel gears.

19. Apparatus according to claim 12 in combination with a syringe having a barrel and plunger of substantially circular cylindrical form.

20. Apparatus according to claim 19 wherein said barrel has an annular flange therearound, and said syringe holding means include a trough formation in said housing to receive at least part of said barrel, said trough having a transverse slot in its side walls for engagement of said flange therein.

21. Apparatus according to claim 12 in combination with a syringe and cannula, said syringe having a fluid outlet terminal in the form of a first annular wall projecting from the syringe barrel with a first closure wall extending thereacross, and said cannula having a fluid input terminal in the form of a second annular wall projecting from one end of the cannula with a second closure wall extending thereacross, one of said closure walls being in the form of a septum of selfsealing elastomeric material, the other one of said closure walls having a hollow needle projecting therethrough, and said annular walls having respectively complimentary conically tapered formations which are co-operable to form a sealed connection with entry of said needle through said septum.

22. Apparatus according to claim 12 in combination with a cannula and cannula needle, said needle having a body with a trailing end which body, towards said trailing end, steps down through a shoulder from one diameter to another, said diameters being respectively substantially the same as the external and internal diameters of said cannula.

23. Apparatus according to claim 12 in combination with a cannula having one end portion of solid form tapered towards its free end, and the associated hollowed portion of said cannula having a short slit adjacent to said one end portion.

24. Apparatus according to claim 12 wherein the teeth of said roller means extend axially across said roller means and are separated from one another circumferentially of said roller means by smooth bottom lands, each of said teeth being of triangular cross-section with an apex angle of about 60° and a negative rake of about 12°.

25. Medicant administration apparatus for feeding medicants over long periods in a continuous manner, comprising: a toothed roller; an electric motor; a transmission operably coupling said gear and motor; a syringe of plastic material including a barrel and a plunger, said plunger having a smooth longitudinal profile; and means releasably holding said syringe in a predetermined disposition relative to said assembly with said plunger extending transversely to the axis of rotation of said roller means and said roller means in penetrated driving engagement with said profile.

* * * * *